(12) United States Patent
McPhearson

(10) Patent No.: US 9,597,475 B2
(45) Date of Patent: Mar. 21, 2017

(54) FAST CONNECT DEVICE FOR OXYGEN HUMIDITY BOTTLES AND OTHER MEDICAL CONTAINERS

(76) Inventor: Jack C McPhearson, Frankton, IN (US)

( * ) Notice: Subject to any disclaimer, the term of this patent is extended or adjusted under 35 U.S.C. 154(b) by 1178 days.

(21) Appl. No.: 13/550,423

(22) Filed: Jul. 16, 2012

(65) Prior Publication Data

US 2013/0014757 A1     Jan. 17, 2013

Related U.S. Application Data

(60) Provisional application No. 61/508,203, filed on Jul. 15, 2011.

(51) Int. Cl.
| | | |
|---|---|---|
| *A61M 16/16* | (2006.01) | |
| *A61M 16/08* | (2006.01) | |
| *A61M 39/10* | (2006.01) | |
| *A61M 11/06* | (2006.01) | |

(52) U.S. Cl.
CPC .... *A61M 16/0816* (2013.01); *A61M 39/1011* (2013.01); *A61M 11/06* (2013.01); *A61M 16/16* (2013.01); *A61M 2039/1027* (2013.01); *A61M 2039/1066* (2013.01)

(58) Field of Classification Search
CPC .............. A61M 16/08; A61M 39/1011; A61M 2039/1027; A61M 2039/1066; F16L 35/00; F16L 35/005
USPC ........ 128/205.24, 205.21; 604/905; 285/277, 285/3, 386, 1, 14
See application file for complete search history.

(56) References Cited

U.S. PATENT DOCUMENTS

| | | | | | |
|---|---|---|---|---|---|
| 2,727,761 | A | * | 12/1955 | Elliott | F16L 37/088 285/277 |
| 2,933,333 | A | * | 4/1960 | Bredtschneider | F16K 1/00 285/354 |
| 2,958,545 | A | * | 11/1960 | Stelzer | F16L 55/1007 285/354 |
| 3,170,667 | A | * | 2/1965 | Szohatzky | F16L 37/23 280/421 |
| 3,201,148 | A | * | 8/1965 | Shurtleff | F16K 13/04 285/3 |
| 3,202,442 | A | * | 8/1965 | Abbey | F16L 29/005 285/3 |
| 3,285,627 | A | * | 11/1966 | Kozulla | F16K 15/144 285/3 |
| 3,334,860 | A | * | 8/1967 | Bolton, Jr. | F16L 37/23 285/277 |

(Continued)

*Primary Examiner* — David E Bochna
(74) *Attorney, Agent, or Firm* — Ritchison Law Offices, PF; John D Ritchison

(57) ABSTRACT

A medical device that is fundamentally a releasable connection system for connecting two sections of tubing together or tubing to a medical device. It includes a male fitting further comprising a male shaft or couple and a female fitting called a socket, both structures having features to permit and provide hygienic connects with the fast or quick retention. The present invention is directed to tubing connection and disconnection apparatus. The device is used for the transport of both gaseous and liquid fluids such as oxygen, air, medicine (liquid or gas) and waste and drainage lines. It provides the medical field speed for a quick reaction to patient needs and the lower cost of the manpower/labor by medical personnel which provides savings opportunities. All this continues to provide reliable, clean and hygienic connections.

10 Claims, 13 Drawing Sheets

(56) References Cited

U.S. PATENT DOCUMENTS

Figure 1D:
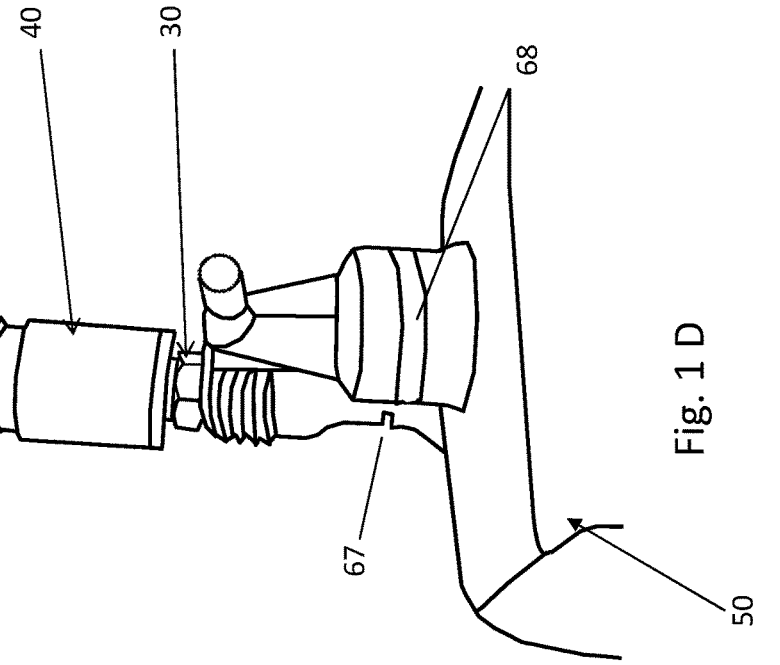
Figure 1C:
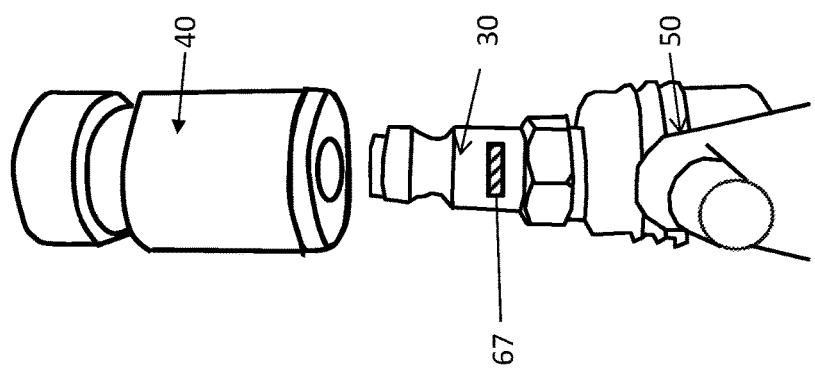
Figure 1A:
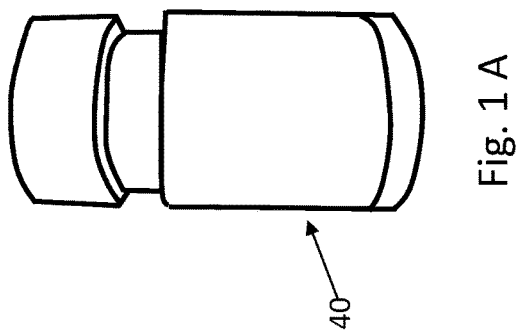
Figure 1B:
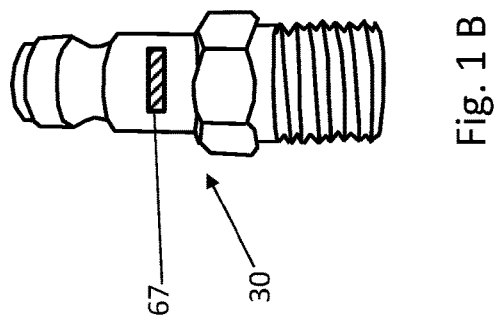

| | | | |
|---|---|---|---|
| 3,391,951 A * | 7/1968 | Miller | F16L 29/005 285/3 |
| 3,466,065 A * | 9/1969 | Acker | F16K 17/403 285/3 |
| 3,484,121 A | 12/1969 | Quinton et al. | |
| 3,532,101 A * | 10/1970 | Snyder, Jr. | F16K 17/40 285/318 |
| 3,852,385 A | 12/1974 | Huggins | |
| 3,873,062 A * | 3/1975 | Johnson | F16L 37/42 285/317 |
| 3,900,223 A * | 8/1975 | Schafer | F16L 29/005 285/4 |
| 4,022,496 A * | 5/1977 | Crissy | F25B 41/003 285/3 |
| 4,052,990 A | 10/1977 | Dodgson | |
| 4,088,436 A * | 5/1978 | Alferes | F16L 37/23 137/517 |
| 4,280,523 A * | 7/1981 | Norton | F16L 37/00 285/3 |
| 4,344,455 A * | 8/1982 | Norton | F16L 37/22 137/329.4 |
| 4,353,488 A * | 10/1982 | Schneiter | B67D 3/045 222/501 |
| 4,436,125 A * | 3/1984 | Blenkush | F16L 37/0841 137/797 |
| 4,541,457 A * | 9/1985 | Blenkush | F16L 37/0841 137/614.05 |
| 4,582,347 A * | 4/1986 | Wilcox | F16L 29/02 285/354 |
| 4,705,303 A | 11/1987 | Van Aspert | |
| 4,792,115 A * | 12/1988 | Jindra | F16L 37/23 137/74 |
| 4,844,513 A * | 7/1989 | St. Louis | F16L 37/23 285/4 |
| 4,974,623 A * | 12/1990 | Sturgis | F16K 17/40 137/74 |
| 5,033,777 A * | 7/1991 | Blenkush | F16L 37/0841 285/317 |
| 5,088,984 A | 2/1992 | Fields | |
| 5,165,728 A * | 11/1992 | Mayer | A61M 39/10 285/316 |
| 5,492,147 A * | 2/1996 | Challender | F16L 29/005 604/905 |
| 5,540,250 A * | 7/1996 | Mullins | F16L 55/1015 137/75 |
| 5,687,712 A * | 11/1997 | Semeia | B63C 11/22 128/205.24 |
| 5,772,261 A | 6/1998 | Magram | |
| 5,971,019 A * | 10/1999 | Imai | F16L 37/23 137/614.04 |
| 6,122,777 A * | 9/2000 | Sage-Passant | E03C 1/021 285/33 |
| 6,997,181 B2 * | 2/2006 | Fletcher | A62B 18/086 128/201.28 |
| 7,153,296 B2 * | 12/2006 | Mitchell | A61M 39/10 604/905 |
| 7,168,428 B1 * | 1/2007 | Zoha | A62B 9/04 128/205.24 |
| 7,390,028 B2 | 6/2008 | Blazek et al. | |
| 8,056,581 B2 * | 11/2011 | Danielson | F16L 37/23 137/614 |
| 8,491,016 B2 * | 7/2013 | Williams | F16L 37/30 285/377 |
| 2005/0167985 A1 * | 8/2005 | Broersma | F16L 35/00 285/417 |
| 2008/0011299 A1 * | 1/2008 | Lucas | A61M 16/10 128/205.24 |
| 2008/0135048 A1 * | 6/2008 | Witt | A62B 9/04 128/205.24 |
| 2009/0261536 A1 | 10/2009 | Beale et al. | |

* cited by examiner

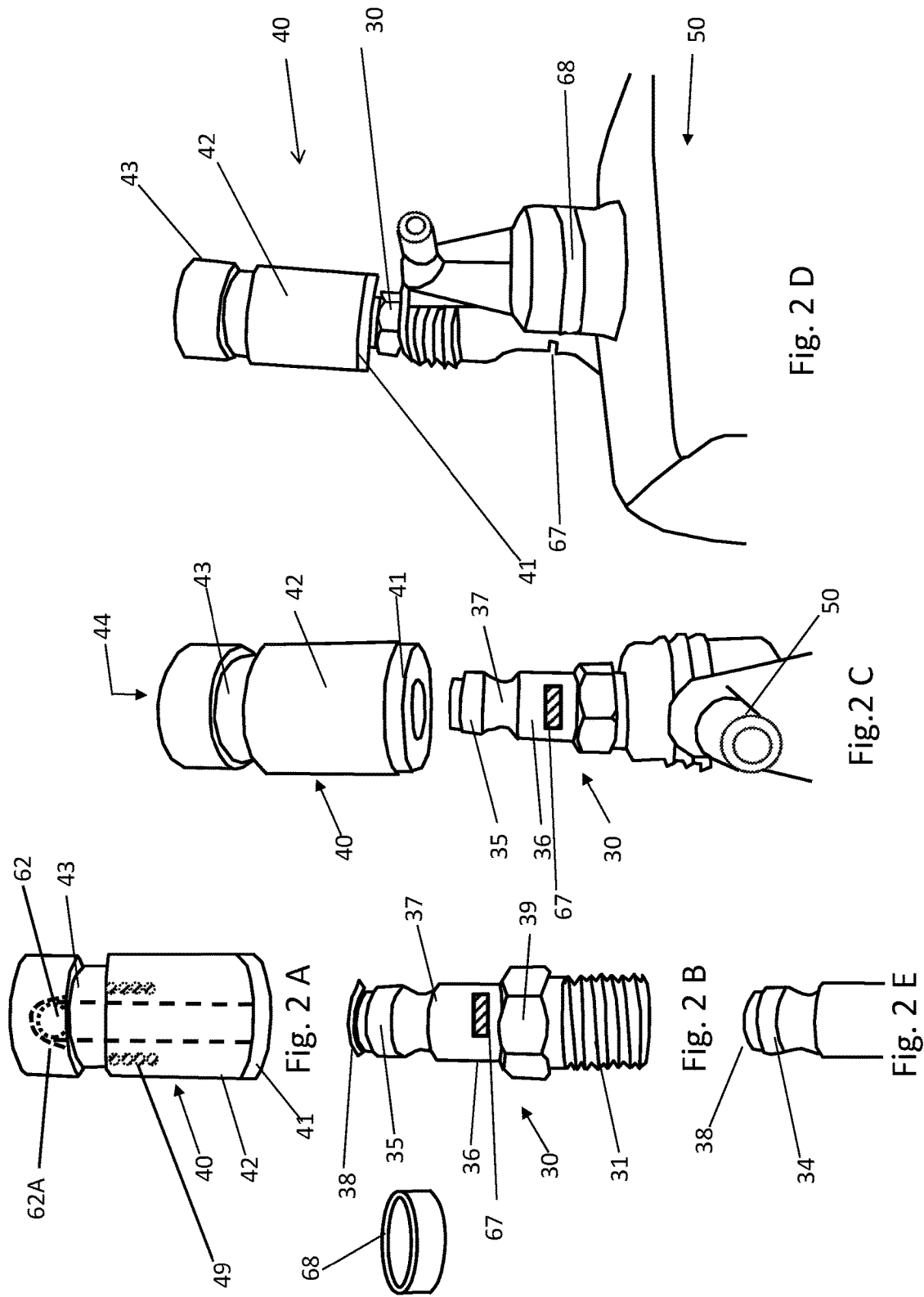

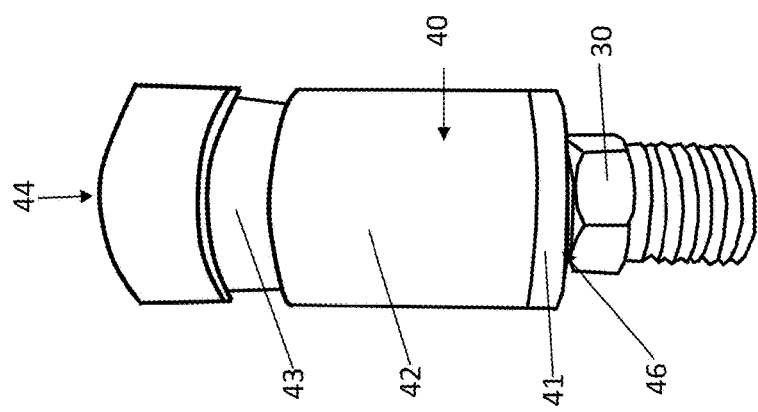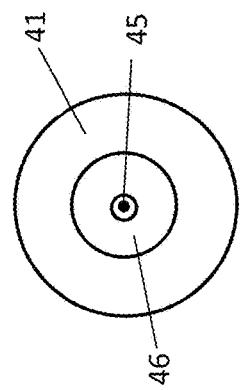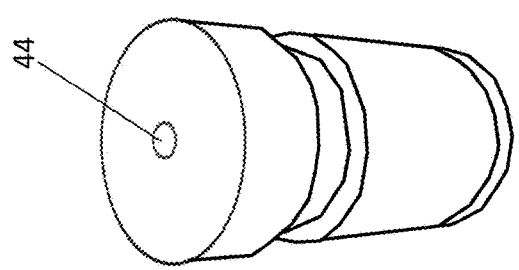

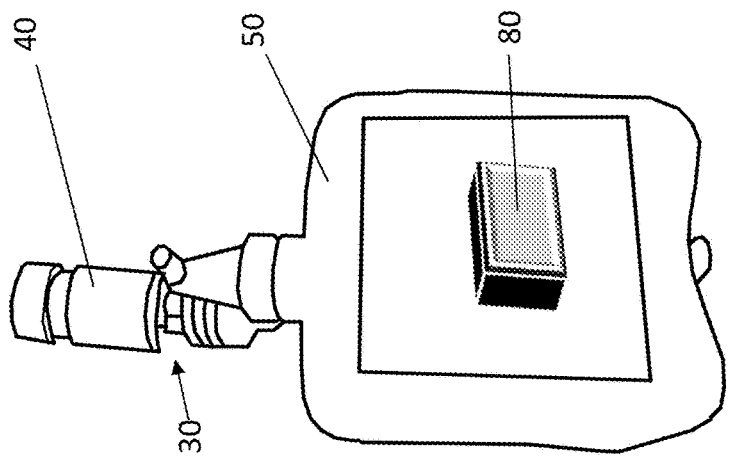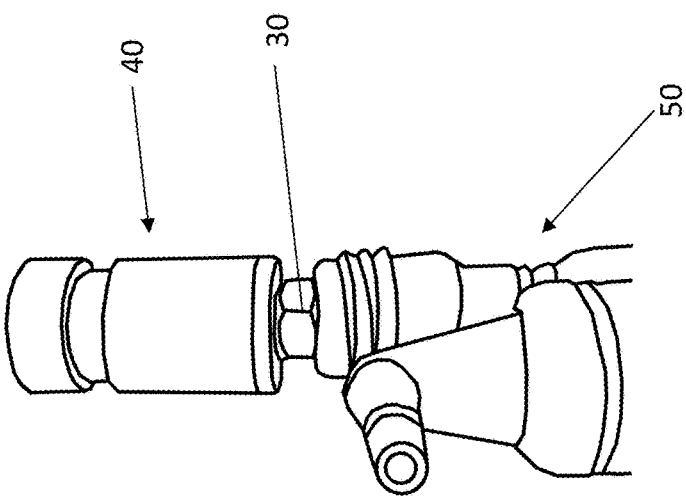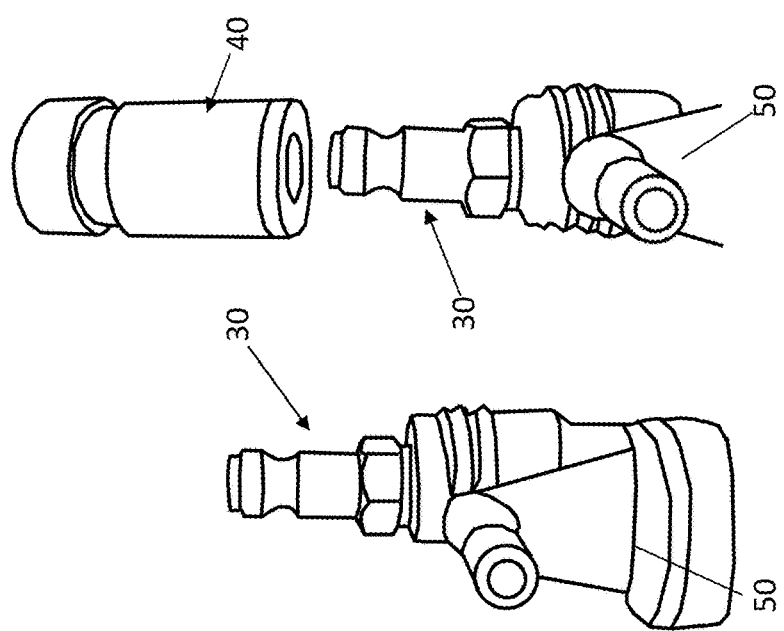

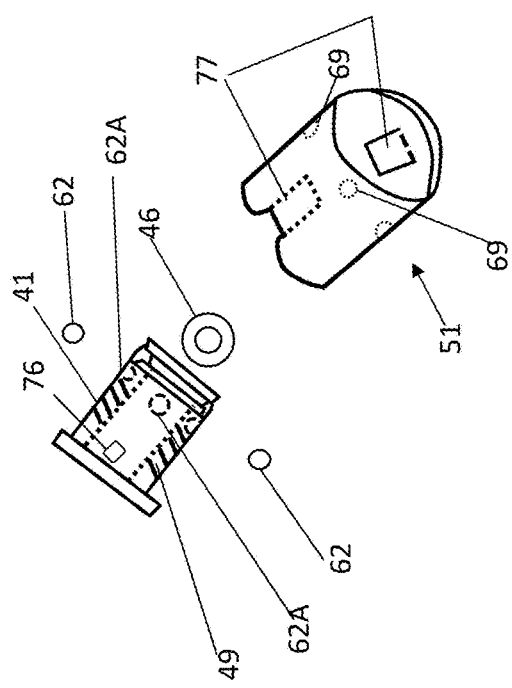
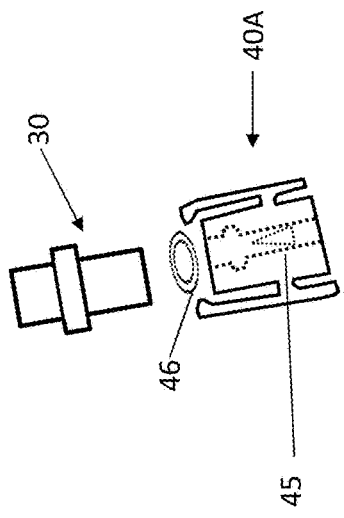
Fig. 10 A
Fig. 10 B

75B

75D

75A

75C

FAST CONNECT DEVICE FOR OXYGEN HUMIDITY BOTTLES AND OTHER MEDICAL CONTAINERS

CROSS-REFERENCE TO RELATED APPLICATIONS

This application claims the benefit of Provisional Patent Application Ser. No. 61/508,203 filed Jul. 15, 2011 by Jack McPhearson and entitled "Fast Connect Device for Oxygen Humidity Bottles and other medical containers".

FIELD OF INVENTION

This invention relates to a Fast Connect Device for Oxygen Humidity Bottles and other medical containers. Particularly this product is related connections of tubes and hoses for medical and hygienic uses where skilled persons connect and reconnect various medical devices with tubes hoses and the like.

Particularly, the Fast Connect Device for Oxygen Humidity Bottles and other medical containers relates generally to the field of medical devices used for the transport of both gaseous and liquid fluids and more specifically to a connection assembly for creating a releasable fluid seal connection between two or more sections of tubing or medical devices. These connections are for oxygen, air, medicine (liquid or gas) and waste and drainage lines. The medical field requires speed for quick reaction to patient needs and the cost of the manpower/labor by skilled technicians and medical personnel provide substantial savings opportunities if some of the tasks to connect medical devices for patient use less labor to complete. All this must of course continue to provide reliable, clean and hygienic connections.

FEDERALLY SPONSORED RESEARCH

Not Applicable.

SEQUENCE LISTING OR PROGRAM

Not Applicable.

BACKGROUND

Field of Invention and Prior Art

As far as known, there are no Fast Connect Device for Oxygen Humidity Bottles and other medical containers or the like. It is believed that this product is unique in its design and technologies.

A. Problems Addressed

Quick release valves utilized in pneumatic systems, as for example valves for connecting lines together to transfer compressed air to air driven tools, have long been known and are in common use. Such valves while well suited for providing for a compressed air or even liquid transfer have posed significant difficulties when they have been applied to medical systems, particularly medical instrument sterilization systems as the valve does not lend itself to reliable cleaning. In such systems, a sterilization agent is transferred into and from a primary sterilization chamber wherein medical instruments are sterilized and is then removable for carrying sterilized instruments to an operating room.

In order to maintain sterility, it is proposed to utilize the fast or quick release device with seals across openings (or apertures) into bottles and on the plugs and sockets of the device. Thus, assuming proper handling procedures, sterility is preserved.

Humidification: This invention relates to improvements in connections to the apparatus for gas humidification systems, particularly systems for humidifying oxygen prior to delivery to a patient. It is well known that the oxygen in conventional supply tanks used by hospitals has a relatively low humidity, and for this reason the oxygen cannot, in many instances, be directly administered to the patient. As a result, the oxygen is frequently passed through humidifiers prior to being delivered through a nasal cannula to the patient. The oxygen or oxygen-containing gas is usually humidified by bubbling the gas through a reservoir of water, saline solution, or other medicated solution.

Intravenous: Tubing sections, for example, medical tubing, must often be joined together to provide for fluid flow (gaseous or liquid) from one medical device to another. It is often desirable, therefore, to connect and disconnect tubing sections from one another. For example, when a patient is provided intravenous fluids, it is often required that an empty fluid bag be replaced with a full fluid bag. It is preferred to merely detach a tubing section connected with the fluid bag to a second tubing section connected with the needle or stent placed intravenously in the patient. In order to switch between the first fluid bag and the second fluid bag, the tubing section connected with the first fluid bag can be disconnected from the second tubing section. The second tubing section can then be easily connected with a tubing section connected with the new fluid bag. This is much simpler than removing the intravenous stent from the patient and replacing it with a new stent directly connected with a new the fluid bag.

Catheter and waste: In other uses, when individuals are hospitalized, or otherwise being treated, it is often necessary that such persons be catheterized, in their urinary tract, both during the hospital stay, and often for extended periods thereafter. Typically, the catheterizations involve the actual catheter, a length of uninterrupted tubing, which terminates in a fitting to a collection bag. Difficulties arise, when the collection bag is full and must be changed, or when switching from a large bag (in-home use) to a smaller bag (for use when moving about or leaving the home). The recuperating patient must either externally clamp or knot the tubing, prior to disconnecting the tubing from the bag and changing the bag.

B. Prior Art

Prior art quick disconnects have been shown in the past, but often are complex and also lack the sterility required for the medical field. A medical device entitled a "Cannula extension and connector apparatus" was issued an U.S. Pat. No. 3,484,121 to Quinton in 1969. Here is taught a cannula extension device that is disclosed which includes a tubular member having a tapered end for insertion into a cannula to provide a turbulent free juncture with the inner wall of the cannula. A protective member secured to the extension device, and in one embodiment integrally formed therewith, covers the end of the cannula to provide a bacteriologically clean joint. A cylindrical shunt connector is described which receives two extension devices and holds the ends thereof in firm end-to-end sealing relationship so that leakage and turbulence of the blood is avoided. The device has several complexly configured pieces and lacks the sterility seal by the McPhearson device. Another device called a "gas humidification apparatus" was issued a U.S. Pat. No. 3,852,385 to Huggins in 1974. This shows an apparatus for administering humidified gas (e.g., oxygen) to a patient that includes a one-piece plastic connector having a tubular portion for connection to an oxygen supply, a tubular spike portion, and a smaller diameter oxygen supply tube within the spike portion and extending beyond the end of the spike portion for first piercing the stopper in an intravenous solution bottle. The spike port enlarges the hole pierced by the oxygen supply tube: The oxygen from the supply tube is delivered to the bottom of the bottle and bubbles upwardly through the liquid therein. The humidified oxygen enters a chamber formed by that part of the bore of the spike portion that is not occupied by the gas tube. The humidified gas then leaves the chamber and enters a conduit on the connector that is connected to a nasal cannula. This is far more parts and complexity in comparison to the McPhearson device. It also lacks the quick connection features.

A third device in the medical field is the "Medico-surgical tube and adaptor" device issued a U.S. Pat. No. 4,052,990 in 1977 to Dodgson. Here is displayed and taught a tubing adaptor of unitary plastics construction that is assembled with an endotracheal or other medico-surgical tube for coupling the tube to a connector or tubing of larger diameter in a gas circuit. The adaptor has a tubular stem which closely fits into the tube and which extends from, and opens through, the base of the cup shape body portion. The cup-shape body portion is for insertion in the passageway of larger diameter to establish the coupling, and the tubular stem is turned back on itself at its open end remote from the base so as to provide an external circumferential claw or lip that is splayed outwardly away from the open end so as to engage with the inside of the tube to restrain withdrawal of the stem from the tube. The claw may be formed by a step which involves the application of force uniformly around the whole circumference of the open end of the stem after that end has been splayed outwardly, against an inclined circumferential shoulder of a spigot. A die coaxial with the spigot is then moved along the spigot into abutment with the portion splayed out on the shoulder to urge this portion back on itself such as to leave the end turned back when the force is removed. This device requires springs and lacks the positive lock features and sterility in the application shown herein. A coupling device was issued an U.S. Pat. No. 4,705,303 in 1987 to van Aspert. The device called a "Detachable hose coupling" shows a coupling that is for rapidly and detachably connecting a conduit pipe or hose to an opening. As disclosed it is provided with an inner sleeve having a flange on at least one end, an outer sleeve capable of moving with little play about the inner sleeve, a groove for a flexible sealing member between the coupling and the opening to be connected as well as clamping means for the relative axial movement of inner and outer sleeve and for pressing the sealing member tightly into the opening. Here the inner sleeve is provided near the flange with an inclined ascending face which can mate with a corresponding ascending face at the outer sleeve. The device Has small mechanical latches and is far more complex than the new device described herein.

Another connector called a "medical connector" was issued a U.S. Pat. No. 5,088,984 in 1992 to Fields. This device teaches a medical connector that as disclosed comprises first and second connector members including a flashback chamber, a needle penetrable into said chamber and an improved one-way valve spaced from said needle for closing the chamber and for establishing fluid communication through the connector when the connector members are joined to administer medication or food to the patient while preventing a patient's blood from entering the chamber and coming in contact with the needle. The device is not applicable for humidification or catheter uses as shown. A simple click and lock device was issued an U.S. Pat. No. 5,772,261 in 1998 to Magram and was entitled "cannula connector and method of connecting medical tubes". This is a method for securing the connection of a medical tube to a port of a fluid transfer instrument. The method provides connections with superior resistance to unexpected disconnection, and thus is particularly beneficial for joining elastic tubes which are implanted within the body for conducting body fluid from one internal location to another or between the body and an external location. The novel method includes inserting a rigid nipple on the port into the lumen of an elastically deformable tube to be joined to the port, placing an initially loose fitting, non-elastically deformable sleeve around the tube on the nipple, and deforming the sleeve radially toward the nipple to clamp the tube between the sleeve and nipple. Unlike the McPhearson device, with this method and apparatus one requires special tools and use of both hands in the procedures.

Another U.S. Pat. No. 7,390,028 was issued in 2008 to Blazek for a "medical tubing quick disconnect apparatus". It is a medical tubing quick disconnect apparatus for connecting two tube ends, that is provided with clamping jaws for shutting off flow through one of the tube ends, to enable separation of the components of the disconnect apparatus. Unlike the McPhearson quick connect, no means for sterility of the apparatus is described. Also, the McPhearson is a less complex clamping/connection system. Finally, in 2009, there was an U S Patent Application Publication US 2009/0261536 by Beale et al called a "quick connect adaptor". This device shows a quick-connect adapter, that is configured to receive an end of a medical tool, is disclosed that it can include a base. A support sleeve can extend from the base having an internal cavity with a first portion defined by a first internal circumferential surface parallel to a major axis of the quick-connect adapter and a second portion defined by a second internal circumferential surface non-parallel to the major axis and generally adjacent to the first portion. A medical tool engagement sleeve can be slidingly disposed within the support sleeve and have a receiving channel and an opening through the engagement sleeve into the receiving channel. The device is considerably more complex with more parts than demonstrated herein by McPhearson.

A full novelty search was completed for this device. As far as known, there are many devices crowded in this field, but no Fast Connect Device for Oxygen Humidity Bottles and other medical containers or the like. It is believed that this product is unique in its design and technologies.

SUMMARY OF THE INVENTION

The present invention is fundamentally a releasable connection system for connecting two sections of tubing together or tubing to a medical device. In one embodiment, the releasable connection assembly for connecting a first section of tubing with a second section of tubing includes a male fitting further comprising a male shaft or couple and a female fitting called a socket, both structures having features to permit and provide hygienic connects with the fast or quick retention. For the preferred embodiment, the connection may be rotatably connected to the male couple to the female socket. The present invention is directed to tubing connection and disconnection apparatus, particular in the environment of medical tubing devices and connections therewith.

The newly invented Fast Connect Device for Oxygen Humidity Bottles and other medical containers may be manufactured at low volumes by very simple means and in high volume production by more complex and controlled systems.

OBJECTS AND ADVANTAGES

There are several objects and advantages of the Fast Connect Device for Oxygen Humidity Bottles and other medical containers. There are currently no known Fast Connect Devices that are effective at providing the objects of this invention.

- It would be desirable to provide a device for enabling the rapid disconnection and re-connection of tubing, such as humidification, intravenous and catheter tubing, for example to facilitate the changing from one container or device to another, whether for replacing a empty/full container, or for switching between medication or devices.
- It would also be desirable to provide such a tubing disconnect apparatus that has a simple and reliable structure and mode of operation, with positive locking when connected.
- It would be further desirable to provide a tubing quick disconnect apparatus that shuts off the flow through the tubing, prior to making the disconnect.
- Another object of the present invention is to provide a quick disconnect valve that is readily broken apart and includes a resilient sleeve as a closure member that can be removed and replaced, and are hygienically sealed.
- An object of this connection device is to provide a fast connection system for gas humidification system that utilizes conventional intravenous solution bottles.
- It is a further and more specific object of the present invention to provide a connector of the type and for the purpose stated that is adapted to puncture a conventional intravenous solution bottle stopper, and wherein the connector provides sterile connections.

The Fast Connect Device for Oxygen Humidity Bottles and other medical containers may:

- permits the fast changing of tubes and devices to allow fast reaction time for patient needs;
- significantly reduce skilled labor time and thus cost in the hospital, nursing home and home care environments; and
- provide sterile devices that may permit more simple packaging.

Finally, other advantages and additional features of the present Fast Connect Device for Oxygen Humidity Bottles and other medical containers will be more apparent from the accompanying drawings and from the full description of the device. For one skilled in the art of fast connection devices and medical field hygiene, it is readily understood that the features shown in the examples with this product are readily adapted to other types of medical connection systems and devices.

DESCRIPTION OF THE DRAWINGS—FIGURES

The accompanying drawings, which are incorporated in and constitute a part of this specification, illustrate an embodiment of the Fast Connect Device for Oxygen Humidity Bottles and other medical containers that is preferred. The drawings together with the summary description given above and a detailed description given below serve to explain the principles of the Fast Connect Device for Oxygen Humidity Bottles and other medical containers. It is understood, however, that the Fast Connect Device is not limited to only the precise arrangements and instrumentalities shown.

FIGS. 1 A through 1 D are sketches of the general fast connect system for medical air, gas and liquid applications devices.

FIGS. 2 A through 2 E are sketches of the fast connect system for medical air, gas and liquid applications devices with components and features noted.

FIGS. 3 A through 3 C are sketches of a prototype sample with the components and features shown from top and side views.

FIGS. 4 A through 4 D are sketches of a prototype sample of a fast connect system for medical air, gas and liquid applications devices in operation on humidifier bottles.

Figure 5:
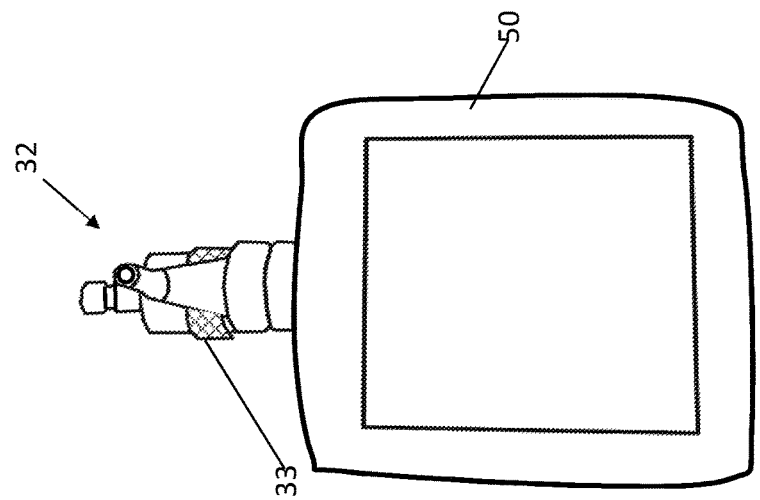
Figure 5:
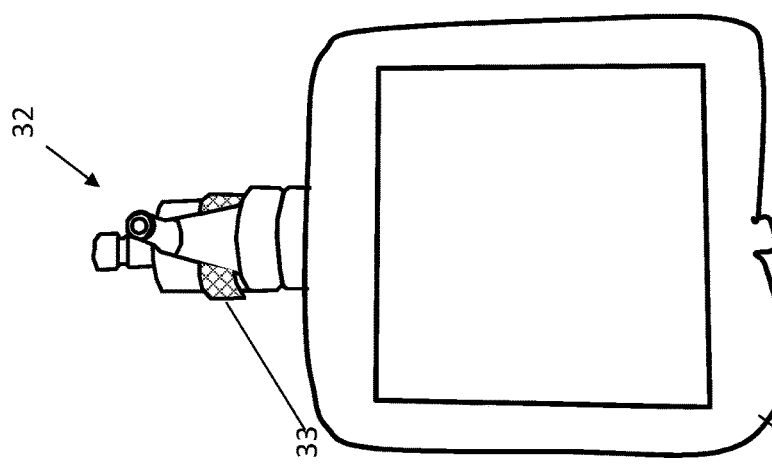
Figure 5:
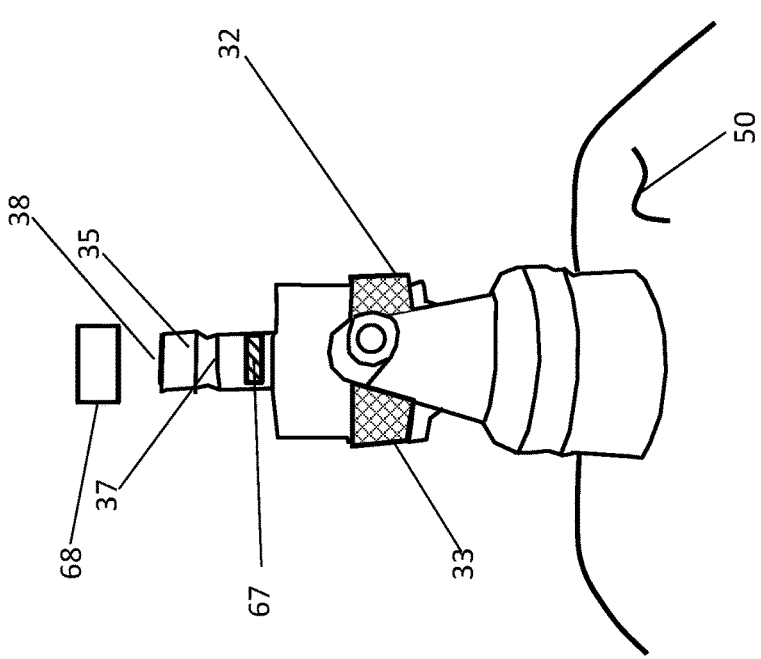

FIGS. 5 A through 5 C are additional sketches of a prototype sample of a fast connect system for medical air, gas and liquid applications devices in operation on humidifier bottles.

Figure 6:
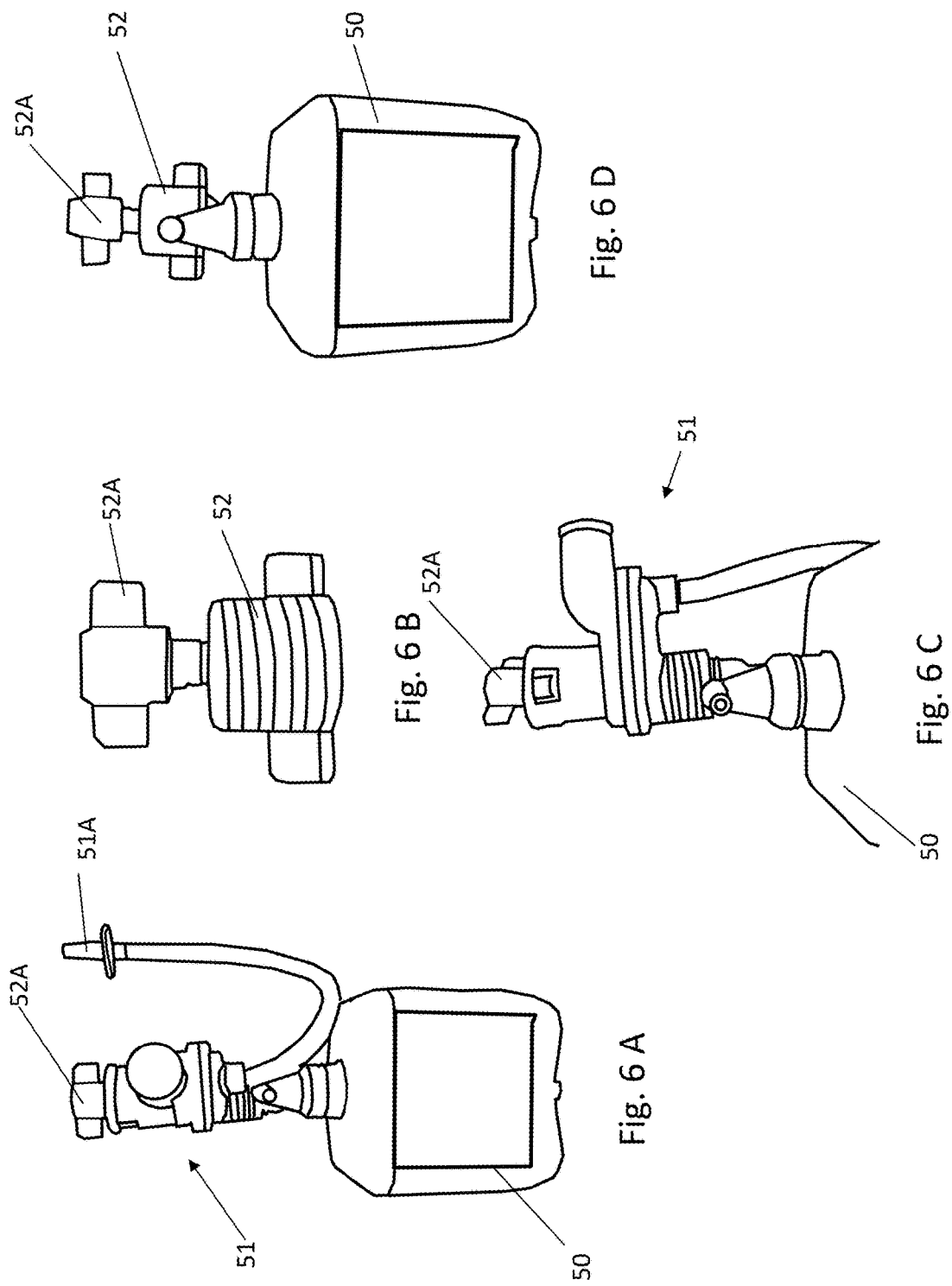

FIGS. 6 A through 6 D are sketches of various common applications with traditional twist and threaded connectors used in the medical field.

Figure 7:
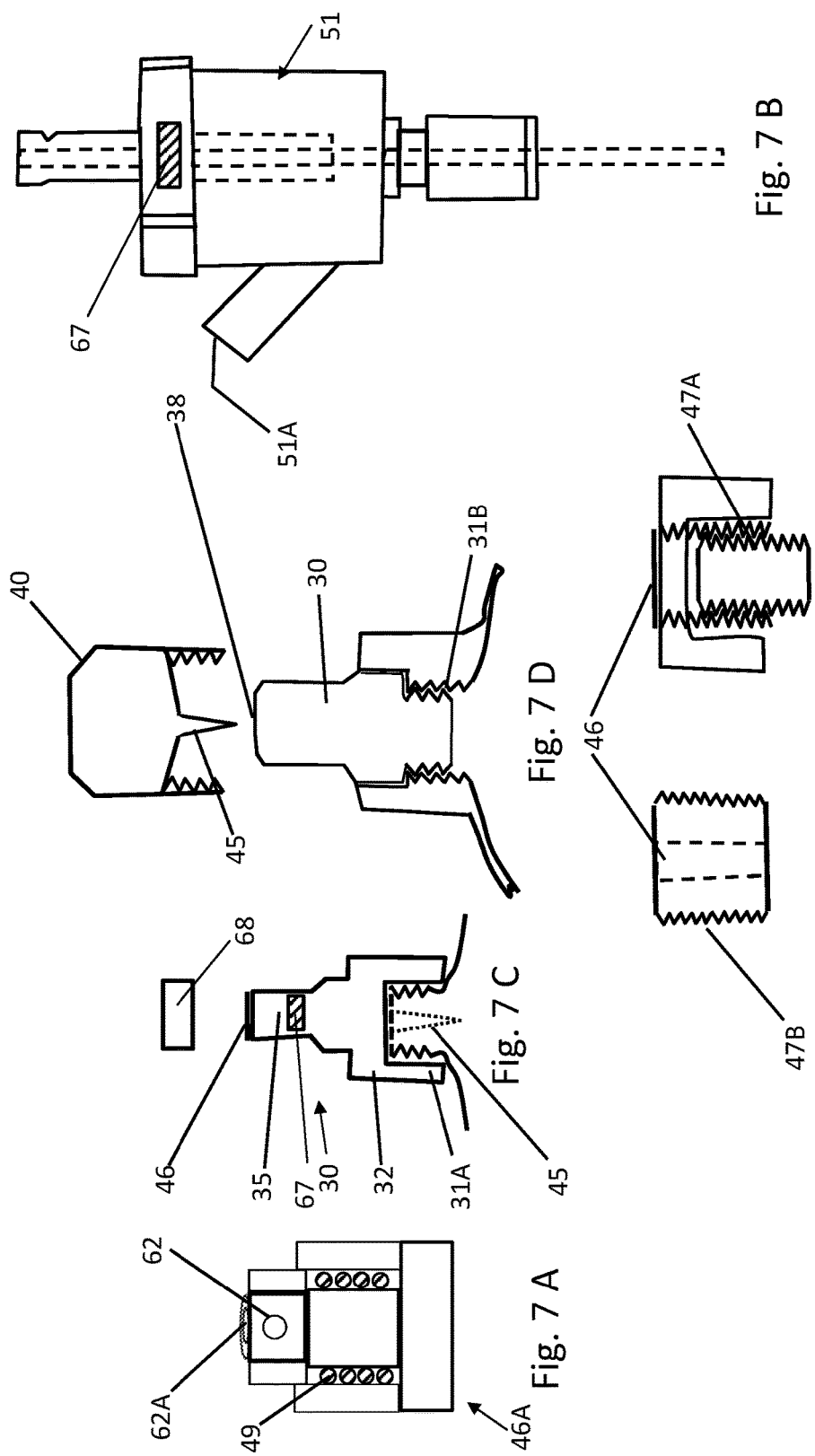

FIGS. 7 A through 7 F are early concept sketches of the fast connect system for medical air, gas and liquid applications devices and how the devices are used.

Figure 8:
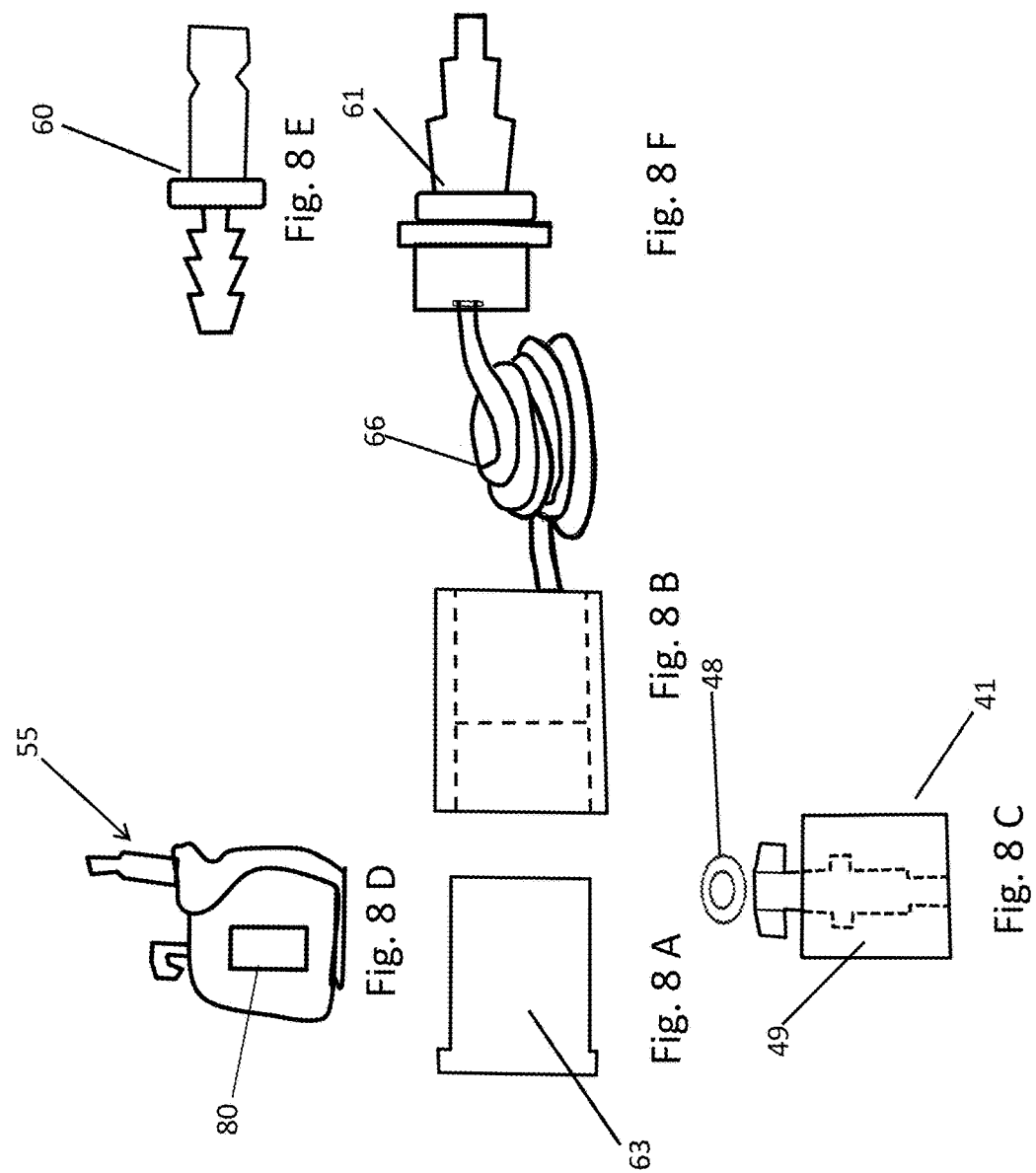

FIGS. 8 A through 8 F are additional early concept sketches of the fast connect system for medical air, gas and liquid applications devices and how the devices are used.

Figure 9:
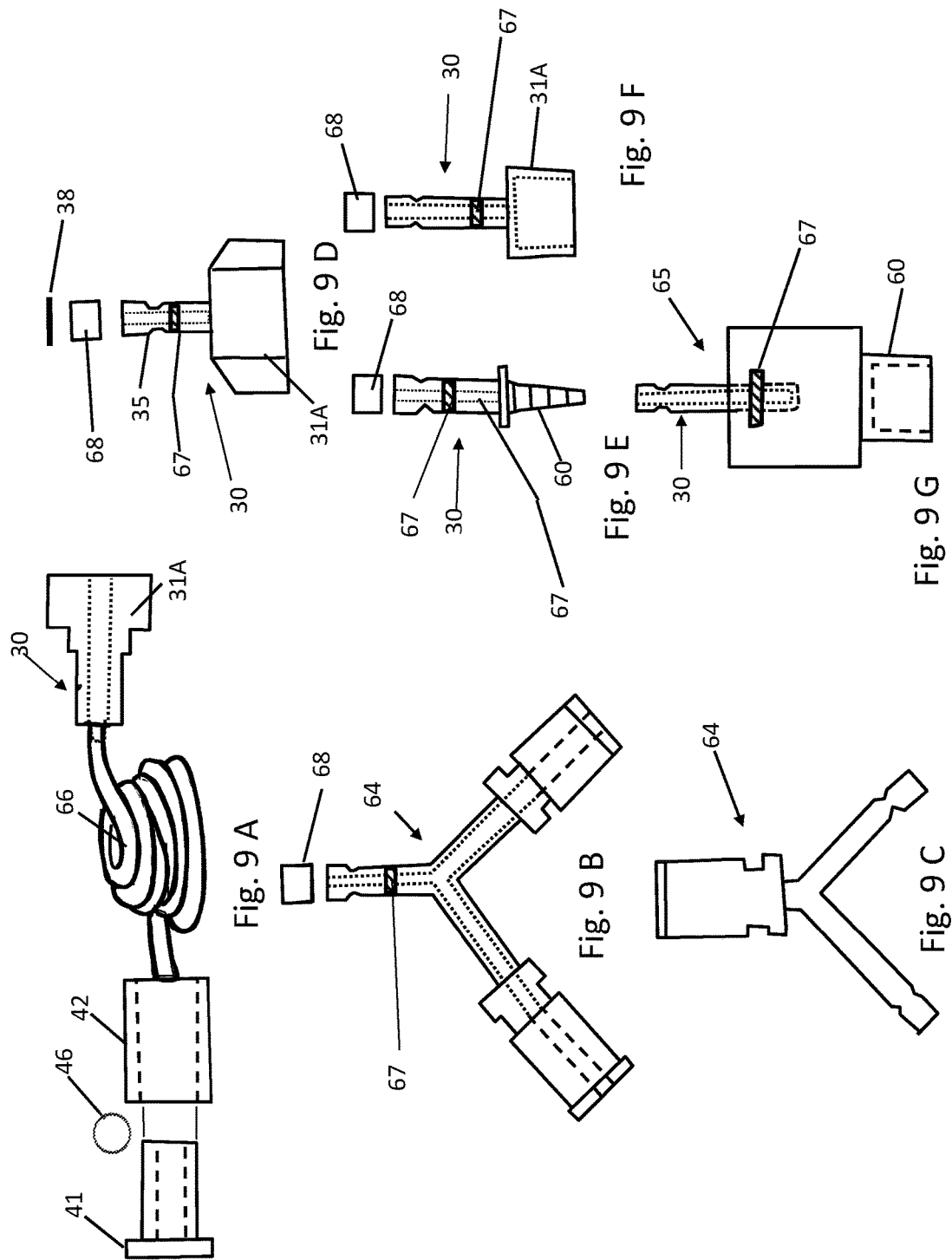

FIGS. 9 A through 9 G are several additional early concept sketches of the fast connect system for medical air, gas and liquid applications devices and how the devices are used.

FIGS. 10 A and 10 B are sketches with added early concept details for the fast connect system for medical air, gas and liquid applications devices.

Figure 11:
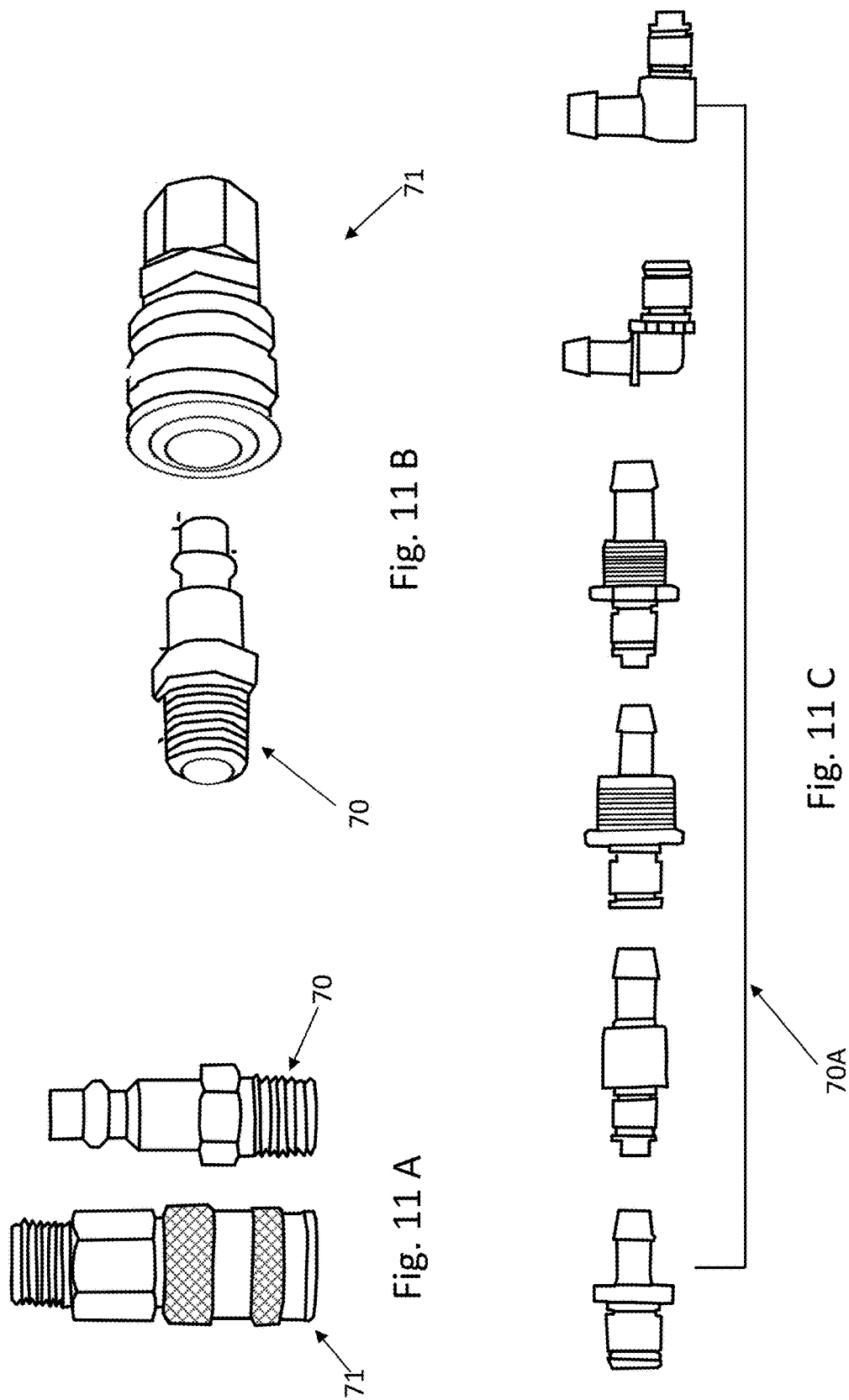

FIGS. 11 A through 11 C are sketches of current quick connects for hoses and equipment used in manufacturing and heavy industrial situations.

Figure 12:
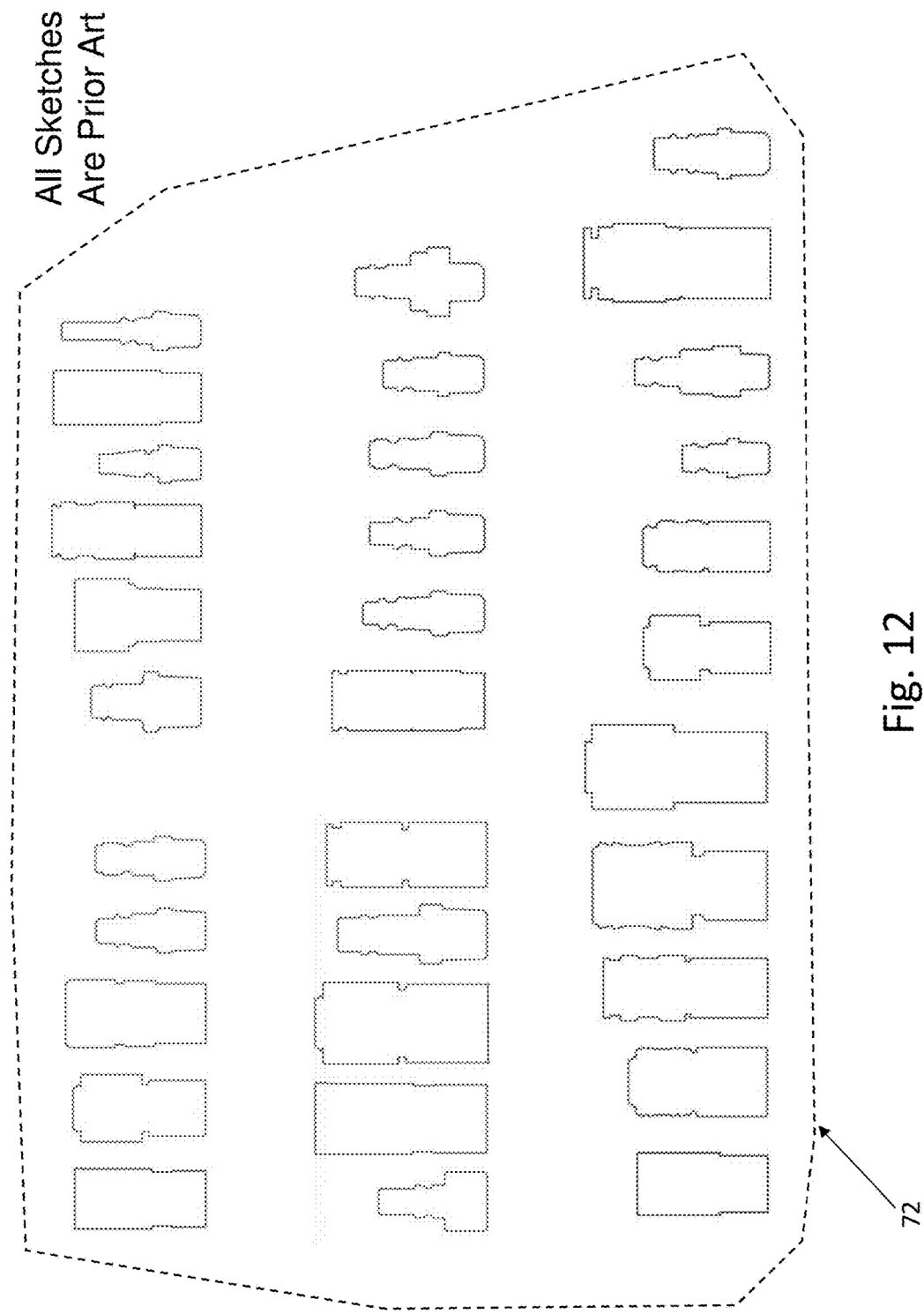

FIG. 12 are sketches of available profiles of quick air connects used in manufacturing and heavy industrial situations.

Figure 13:
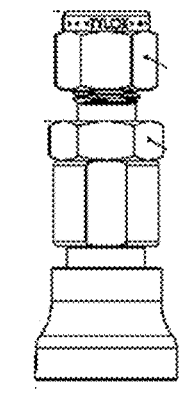
Figure 13:
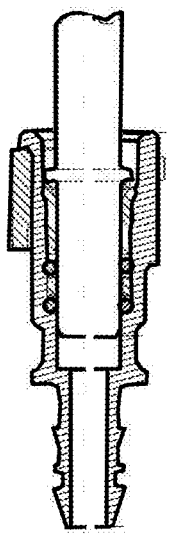
Figure 13:
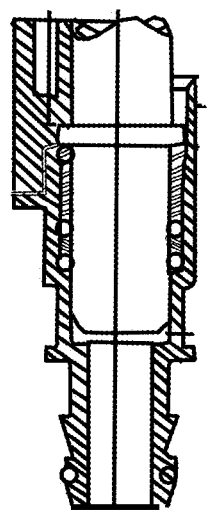
Figure 13:
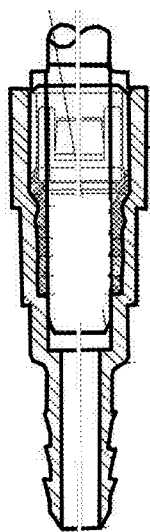

FIGS. 13 A through 13 D are sketches of prior art quick connects for manufacturing and heavy industrial uses.

DESCRIPTION OF THE DRAWINGS—REFERENCE NUMERALS

The following list refers to the drawings:

TABLE B

Reference numbers

| Ref # | Description |
|---|---|
| 30 | Male Quick Connect Plug |
| 31 | Means For Connecting to a medical device |
| 31A | External Means For Connecting to a medical device |
| 31B | Internal Means For Connecting to a medical device |
| 32 | Alternative Means For Connecting |
| 33 | Encasement Means (means for encasing the device) |
| 34 | Sealant groove (groove, labyrinth and the like) |
| 35 | Couple Plug |
| 36 | Couple Barrel |
| 37 | Seal Surface |

TABLE B-continued

Reference numbers

| Ref # | Description |
|---|---|
| 38 | Seal Cover |
| 39 | Tool Flats |
| 40 | Female Receiver Socket |
| 41 | Base |
| 42 | Moveable Sleeve |
| 43 | Body |
| 44 | Aperture For Hose, Tube, etc. |
| 45 | Means For Puncture (means for puncturing the hygienic seal) |
| 46 | Socket Aperture For Plug |
| 46A | Surface Seal |
| 47 | Means for Connecting the quick connect device to a Medical Device |
| 47A | External Means for Connecting the quick connect device to a Medical Device |
| 47B | Internal Means for Connecting the quick connect device to a Medical Device |
| 48 | Plug Seal |
| 49 | Spring |
| 50 | Medical Device Such As A Humidifier Water Bottle |
| 51 | Nebulizer |
| 51A | Medicine Venturi Line |
| 51B | Tube Connector |
| 52 | Traditional Cap |
| 52A | Trade Cap Tube Connector |
| 55 | Humidifier Bottle |
| 60 | Tube Connector |
| 61 | Hose Connector |
| 62 | Locking balls or alternatively Molded ball locks to removably secure |
| 62A | Aperture to hold locking balls 62 |
| 63 | Alternative Connection Socket |
| 64 | Y Connector |
| 65 | Venturi Combination |
| 66 | Hose, Tube, Elongated Conductor For Gas, Oxygen, Air, Fluids, Waste |
| 67 | Whistle slit in a device or tube |
| 68 | Alarm band (various colors for the specific pressure) |
| 69 | molded hemispheres (detent pocket) to receive balls 62 |
| 70 | Traditional Plug |
| 70A | Plastic Plug |
| 71 | Traditional Socket |
| 72 | Plug and socket Variation profiles/outlines |
| 75A | Prior Art - ½ inch quick connect by Stan Pro of Novi, Michigan Posi-Lock ™ Part No. 75003092 |
| 75B | Prior Art - 5/16 inch quick connect by Stan Pro of Novi, Michigan "Q" style Part No. 75003058 |
| 75C | Prior Art - 5/16 inch quick connect by Stan Pro of Novi, Michigan Posi-Lock ™ style Part No. 75003057 |
| 76 | Lock slot |
| 77 | Lock tab |
| 80 | Low Fluid alarm device |

DETAILED DESCRIPTION OF PREFERRED EMBODIMENT

This present device relates to a Fast Connect Device for Oxygen Humidity Bottles and other medical containers. Particularly this product is related connections of tubes and hoses for medical and hygienic uses where skilled persons connect and reconnect various medical devices with tubes hoses and the like. Particularly, the Fast Connect Device for Oxygen Humidity Bottles and other medical containers relates generally to the field of medical devices used for the transport of both gaseous and liquid fluids and more specifically to a connection assembly for creating a releasable fluid seal connection between two or more sections of tubing or medical devices. These connections are for oxygen, air, medicine (liquid or gas) and waste and drainage lines.

Taught here are the ways a Fast Connect Device for Oxygen Humidity Bottles and other medical container may be used in the medical field for various advantages. The advantages for the Fast Connect Device are that the device may permit the fast changing of tubes and devices to allow fast reaction time for patient needs; significantly reduce skilled labor time and thus cost in the hospital, nursing home and home care environments; and provide sterile devices that may permit more simple packaging.

The preferred embodiment of the Fast Connect Device is fundamentally a releasable connection system for connecting two sections of tubing together or tubing to a medical device.

In one embodiment, the releasable connection assembly for connecting is made of a first section of tubing with a second section of tubing includes a male fitting further comprising a male shaft or couple and a female fitting called a socket, both structures having features to permit and provide hygienic connects with the fast or quick retention. For the preferred embodiment, the connection may be rotatably connected to the male couple to the female socket. The present invention is directed to tubing connection and disconnection apparatus, particular in the environment of medical tubing devices and connections therewith.

The device may be made of durable materials that may be machined, molded, or cast. These materials may be metal such as brass, steel, stainless steel, aluminum or other metals; composite materials such as plastics like nylon, urethane, polypropylene and the like; or other suitable materials that are durable and able to be hygienically manufactured.

There is shown in FIGS. 1-13 a complete description and operative embodiment of the Fast Connect Device for Oxygen Humidity Bottles and other medical containers. In the drawings and illustrations, one notes well that the FIGS. 1-3 and 7-10 demonstrate the general configuration of this product. The operation and use is shown in FIGS. 4 and 5. Background and prior art is shown in FIGS. 6 and 11-13. The description, operation and background are described in detail below.

The accompanying drawings, which are incorporated in and constitute a part of this specification, illustrate an embodiment of the Fast Connect Device for Oxygen Humidity Bottles and other medical containers that is preferred. The drawings together with the summary description given above and a detailed description given below serve to explain the principles of the Fast Connect. It is understood, however, that the device is not limited to only the precise arrangements and instrumentalities shown. Other examples of quick and fast connections of tubes, hoses and the like for medical needs and uses are still understood by one skilled in the art of fast connections in the medical field and these other examples and equivalent products are to be fully considered within the scope and spirit shown here.

FIGS. 1 A through 1 D are sketches of the general fast connect system for medical air, gas and liquid applications devices. Shown are the general male quick connect or plug 30, the female receiver or socket 40 and a medical device such as a bottle 50 for use with the device.

FIGS. 2 A through 2 E are sketches of the fast connect system for medical air, gas and liquid applications devices with components and features noted. In FIG. 2 A is the female socket 40 wherein the female fitting called a socket has an aperture throughout the entire length. It has the components and features of the socket base 41, the movable sleeve 42, and the socket body 43. FIG. 2 B is the male plug 30 with an aperture throughout the entire length and with special features. It is comprised at one end, the couple end or plug 35, an end seal 38 (that is secured tightly against the surface around the aperture in the socket); the couple barrel 36 (that slides internal to the socket base) and a surface for sealing 37 (optional seal like an O-ring or an equivalent may be placed here, but more traditionally the seal is in the socket), a tooled flat 39 for ease of handling, and at the other end a Means For Connecting to a medical device (external or internal connection means . . . such as a threaded connection, clip, twist lock or a plethora of other connection means well known to those skilled in the art of medical devices. The surface for sealing on the plug is to permit a contiguously, tight contact to the female fitting. FIG. 2 C repeats the plug 35 and socket 40 being assembled in place with a container 50. One notes that the balls 62, ball retention apertures 62A in the body and/or sleeve, and spring 49 between the body and sleeve which are typical of a quick connection couple are internal to the movable sleeve 42. FIG. 2 D shows the device with the plug 30 and socket 40 now coupled and removably mounted/secured with the bottle 50. One notes that as the plug is placed into the bottle, the plug pierces the hygienically sealed bottle containing the sterile water, or medicine, etc. As will be discussed later, one embodiment anticipates the device plug 30 or 40 being insert-molded into the bottle 50. FIG. 2 E repeats part of the plug 30 with the alternative groove 34 shown. This groove 34 may hold an O-ring (not shown here) to improve a seal with the interior surface of the socket 40 (body) aperture 46 (see FIG. 3 A).

FIGS. 3 A through 3 C are sketches of a prototype sample with the components and features shown from top and side views. FIGS. 2 A and 2 B are shown for reference on the sheet. FIG. 3 A shows the bottom view of the sleeve 41. The aperture 46 is indicated. This is where the plug 30 enters the socket 40 (into the machined or molded body). Also noted is the means 45 for puncturing the seal 38 on the plug 30. Hence, the water can now travel through to the tubing and the entire system's sterility or hygiene has been preserved. FIG. 3 B indicates the top of the socket 40 where the tube (not shown) enters the aperture 44.

In FIG. 3 C a side view of the assembly of the socket 40 and plug 40 is shown with the features and components that have been previously described in the above paragraphs.

FIGS. 4 A through 4 D and FIGS. 5 A through 5 C are described below with the operation and use.

FIGS. 6 A through 6 D are sketches of various common applications with both traditional twist and threaded connectors used in the medical field. FIG. 6 A shows a nebulizer 51 with a twist cap 52 for connection to a tube at the connector 52A. FIG. 6 B shows a threaded or twist traditional cap 52 with the tube connector 52A. These require a nurse or technician to prep the humidifier bottles 51 and connect the various components. This takes valuable medical personnel reaction time for helping the patient as well as the labor expense when using the skilled personnel. FIGS. 6 C and 6 D show other traditional medical devices with the high-labor intensive threaded and twist-on caps.

FIGS. 7 A through 7 F are early concept sketches of the fast connect system for medical air, gas and liquid applications devices and how the devices are used. FIG. 7 A shows an alternative socket device 46A. One notes that the balls 62, retention apertures 62A, and spring 49 which are typical of a quick connection couple are internal to the movable sleeve 42. FIG. 7 B is a nebulizer 51 with a medicine venturi line 51A and a tube connecter 51B. FIG. 7 C shows an alternative base with plug 32 connection for a plug 30 such as an external means 31A. It still has a male plug 35 to interconnect and seal with the socket 40. FIG. 7 D shows the device with an alternative connection means 31B with an internal means to connect. These may be insert molded (for thermoplastic) features to connect with the bottles 50 or other medical devices. Note also the seal 38 across the aperture of the plug 35. This seal 38 will be punctured by the puncture means 45 (such as an extended, tapered "to a point" extension of the socket material inside the socket or as an alternative a secondary, separate tapered and elongated post placed into a small aperture in the socket) in the socket 40 device. In FIGS. 7 E and 7 F, the internal 47B and external 47A means to secure a socket 40 to a device 50 is shown as a conceptual sketch.

FIGS. 8 A through 8 F are additional early concept sketches of the fast connect system for medical air, gas and liquid applications devices and how the devices are used. An alternative socket concept 63 with the seal 48, spring 49, and release base 41 are shown. Likewise a humidifier bottle 55 is shown as well as a tube connector 60 and hose connector 61. Further the representation of a hose or tube 66 is shown. Note that on FIG. 8 D and FIG. 4 D the medical bottle 50 shows an alarm device 80 incorporated to sense the low water/fluid condition. This sensor 80 and bottle 50 combination is not anticipated by prior art.

FIGS. 9 A through 9 G are several additional early concept sketches of the fast connect system for medical air, gas and liquid applications devices and how the devices are used. FIG. 9 A is the connection device with most of the components and features already shown and described. FIGS. 9 B and 9 C are demonstrations of a "WYE" 64 or 2 to 1 connection device. FIG. 9 D shows an externally connected 31A plug 35 associated with a pressure relief means incorporated to the tube connector. FIG. 9 E shows a plug 30 with a tube connector 60. FIG. 9 F shows a plug 30 connection with a ventilator. In FIGS. 9 D, E and F demonstrate the use of a whistle slot 67 manufactured into the body of plug 30. The slot 67 can then be encircled and sealed by an elastic band 68. This band 68 may be varied in strength to expand when the pressure exceeds a pre-determined value. Therefore the band may permit various pressures to create and alarm when it exceeds the value and permits the gas to pass through/across the whistle slot 67 and create an alarm. The elastic bands 68 could be color coded to coordinate with a pressure value for the alarm. The slot FIG. 9 G shows an air and oxygen mixer device without a medicine venturi connection.

FIGS. 10 A and 10 B are sketches with added early concept details for the fast connect system for medical air, gas and liquid applications devices. Here the various components as described above are again shown and indicated in the drawings. FIG. 10 A also shows the lock tab 77 and locking slot 76 system to create an even greater security of the connection device. One notes that the balls 62, retention apertures 62A, and spring 49 which are typical of a quick connection couple are internal to the movable sleeve 42. This is similar to the description in FIG. 2 in the above paragraphs. One skilled in the art of molded devices well appreciates the orientation of the tabs and slots may be longitudinal along the axis of the device or latitudinal or another angularity and still be within the scope and spirit of the locking features. The longitudinal drawing is exemplary and not limiting to this unique locking system within the overall fast connection devices. The other unique features are the molded balls 62 molded into the interior structure and the hemispheric detent pockets 69 placed in and around the sleeve. This permits a detent lock when the balls 62 are rotated into place with the pockets 69. This creates a secure connection which may be removed with successive twist of the two pieces.

FIGS. 11 A through 11 C are sketches of current quick connects for hoses and equipment used in manufacturing and heavy industrial situations. A standard couple 70 and socket 71 is shown. The parts and features are shown in FIG. 11 B. In FIG. 11 C, various molded plastic components 70A used in manufacturing are demonstrated.

FIG. 12 are sketches of examples of the available plethora of profiles 72 of quick air connects used in manufacturing and heavy industrial situations.

FIGS. 13 A through 13 D are sketches of prior art quick connects 75 A, B, and C for manufacturing and heavy industrial uses. First shown is a ½ inch quick connect 75A by Stan Pro of Novi, Michigan Posi-Lock™ Part No. 75003092. Next is a ⅝ inch quick connect 75B by Stan Pro of Novi, Michigan "O" style Part No. 75003058. Finally a ⅝ inch quick connect 75C by Stan Pro of Novi, Michigan Posi-Lock™ style Part No. 75003057. All are industrial examples of quick connect style couplings.

The details mentioned here are exemplary and not limiting. Other specific components and manners specific to describing a Fast Connect Device for Oxygen Humidity Bottles and other medical containers may be added as a person having ordinary skill in the field of fast tubing connection devices in the medical field and their uses well appreciates.

Operation of the Preferred Embodiment

The Fast Connect Device for Oxygen Humidity Bottles and other medical containers has been described in the above embodiment. The manner of how the device operates is described below. One may note well that the description above and the operation described here must be taken together to fully illustrate the concept of the Fast Connect Device for the medical field. The preferred embodiment was described above.

The Fast Connect Device operates somewhat similar to a traditional quick connect device known to industry. The sockets 40 and plugs 30 are quickly snapped into place. Either or both of the parts—the socket 40 and plug 30—may be connected to the hose 66 or the device 50. However, the use is not currently available in the medical field and the features to permit hygienic use with the fast connection has not been effectively addressed by prior art in or out of the field. Therefore the new use of this device with various combinations and added features is not obvious to an ordinary person skilled in the art of quick connecting devices and the like.

Many uses are anticipated for the Fast Connect Device. Some examples, and not limitations, are shown in the following Table.

| ITEM | DESCRIPTION |
|---|---|
| 1 | Humidification systems for air and oxygen |
| 2 | Intravenous connections for providing blood and medications |
| 3 | Bodily Waste and urine connections for catheters, surgical drains, excrement devices (colostomy, etc) and the like. |

FIGS. 4 A and 4 D are sketches of a prototype sample of a fast connect system for medical air, gas and liquid applications devices in operation on humidifier bottles. The plug 30 is internally insert molded into the bottle or other medical device. From there, the device may be interconnected with the socket 40 and quickly connect hoses or tubes 66. As the socket connects to the plug, the seal 38 on the plug 30 is pierced by the means to puncture 45 attached with the socket 40. Thereby, the bottle and any contents is maintained in a sterile condition until use. Note that on FIG. 4 D the medical bottle 50 shows an alarm device 80 incorporated to sense the low water/fluid condition. This sensor 80 and bottle 50 combination is not anticipated by prior art.

FIGS. 5 A and 5 C are additional sketches of a prototype sample of a fast connect system for medical air, gas and liquid applications devices in operation on humidifier bottles. The same discussion of the features above are continued here. However, shown here is an externally molded insert 32 for connecting the plug 30 to the bottle 50.

While certain novel features of this invention have been shown and described and are pointed out in the annexed claims, it is not intended to be limited to the details above, since it will be understood that various omissions, modifications, substitutions and changes in the forms and details of the device illustrated and in its operation can be made by those skilled in the art without departing in any way from the spirit of the present invention. Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

Unless defined otherwise, all technical and scientific terms used herein have the same meaning as commonly understood by one of ordinary skill in the art to which these inventions belong. Although any methods and materials similar or equivalent to those described herein can also be used in the practice or testing of the present inventions, the preferred methods and materials are now described above in the foregoing paragraphs.

Other embodiments of the invention are possible. Although the description above contains much specificity, these should not be construed as limiting the scope of the invention, but as merely providing illustrations of some of the presently preferred embodiments of this invention. It is also contemplated that various combinations or sub-combinations of the specific features and aspects of the embodiments may be made and still fall within the scope of the inventions. It should be understood that various features and aspects of the disclosed embodiments can be combined with or substituted for one another in order to form varying modes of the disclosed inventions. Thus, it is intended that the scope of at least some of the present inventions herein disclosed should not be limited by the particular disclosed embodiments described above.

The terms recited in the claims should be given their ordinary and customary meaning as determined by reference to relevant entries (e.g., definition of "plane" as a carpenter's tool would not be relevant to the use of the term "plane" when used to refer to an airplane, etc.) in dictionaries (e.g., widely used general reference dictionaries and/or relevant technical dictionaries), commonly understood meanings by those in the art, etc., with the understanding that the broadest meaning imparted by any one or combination of these sources should be given to the claim terms (e.g., two or more relevant dictionary entries should be combined to provide the broadest meaning of the combination of entries, etc.) subject only to the following exceptions: (a) if a term is used herein in a manner more expansive than its ordinary and customary meaning, the term should be given its ordinary and customary meaning plus the additional expansive meaning, or (b) if a term has been explicitly defined to have a different meaning by reciting the term followed by the phrase "as used herein shall mean" or similar language (e.g., "herein this term means," "as defined herein," "for the purposes of this disclosure [the term] shall mean," etc.). References to specific examples, use of "i.e.," use of the word "invention," etc., are not meant to invoke exception (b) or otherwise restrict the scope of the recited claim terms. Other than situations where exception (b) applies, nothing contained herein should be considered a disclaimer or disavowal of claim scope. Accordingly, the subject matter recited in the claims is not coextensive with and should not be interpreted to be coextensive with any particular embodiment, feature, or combination of features shown herein. This is true even if only a single embodiment of the particular feature or combination of features is illustrated and described herein. Thus, the appended claims should be read to be given their broadest interpretation in view of the prior art and the ordinary meaning of the claim terms.

Unless otherwise indicated, all numbers or expressions, such as those expressing dimensions, physical characteristics, etc. used in the specification (other than the claims) are understood as modified in all instances by the term "approximately." At the very least, and not as an attempt to limit the application of the doctrine of equivalents to the claims, each numerical parameter recited in the specification or claims which is modified by the term "approximately" should at least be construed in light of the number of recited significant digits and by applying ordinary rounding techniques.

With this description it is to be understood that the Fast Connect Device for Oxygen Humidity Bottles and other medical containers is not to be limited to only the disclosed embodiment of product. The features of the device are intended to cover various modifications and equivalent arrangements included within the spirit and scope of the description.

What is claimed is:

1. A fast tube and hose connection couple device made of durable materials and comprising
   (a) a male fitting plug with an aperture throughout the entire length comprising a male side of a couple;
   (b) a female socket with an aperture throughout the entire length comprising a female side of a couple;
   (c) the male fitting plug device further comprising
   at one end, the male fitting plug;
   an end seal across the aperture;
   a couple barrel that slides internal to a socket base and the barrel has a surface for sealing contiguously to a female fitting;
   a tooled flat for ease of handling; and
   at the other end a means for connecting the male fitting plug to a medical device;
   a whistle slot(67); and
   an elastic band (68) wherein the connection couple device is fundamentally a releasable connection system for connecting two sections of tubing together or tubing to a medical device and the couple device may be used for oxygen humidity bottles and other medical devices to ensure a fast, secure and hygienic connection for air, gas and liquid applications in medical applications
   and wherein the whistle slot (67) and band (68) provide a quick bleed and release of pressure in the medical device.

2. The fast tube and hose connection couple device according to claim 1 wherein the means for connecting the male fitting plug is from the group consisting of an external threaded connection, an internal threaded connection, a spring clip, a twist lock, and a press fit.

3. The fast tube and hose connection couple device according to claim 1 wherein the means for connecting the male fitting plug to a plastic bottle is by insert molding the male fitting plug into the bottle.

4. The fast tube and hose connection couple device according to claim 1 wherein the barrel surface is further comprised of a groove encircling the barrel which secures an o-ring.

5. The fast tube and hose connection couple device according to claim 1 wherein the other medical device is from a group consisting of a humidifier bottle, a venturi, a ventilator, intravenous connectors, urine devices, bodily waste devices, and surgical waste devices.

6. The fast tube and hose connection couple device according to claim 1 wherein the durable material is from a group consisting of brass, steel, alloy steel, stainless steel, and aluminum.

7. The fast tube and hose connection couple device according to claim 1 wherein the durable material is a composite material.

8. The fast tube and hose connection couple device according to claim 7 wherein the composite material is from a group consisting of a plastic, nylon, urethane, and polypropylene.

9. The fast tube and hose connection couple device according to claim 1 wherein the medical bottle is comprised of an alarm device incorporated to sense a low water/fluid condition.

10. A fast tube and hose connection device made of durable materials and comprising
    (a) a male fitting plug with an aperture throughout the entire length and comprised of
    (i) at one end, a plug;
    (ii) an end seal across the aperture;
    (iii) a couple barrel that slides internal to a socket base and the barrel has a surface for sealing contiguously to a female fitting;
    (iv) a tooled flat for ease of handling; and
    (v) at the other end a means for connecting the male plug to a medical device;
    (vi) a whistle slot(67); and
    (vii) an elastic band (68) and
    (b) a female fitting called a socket with an aperture throughout the entire length comprised of
    (i) a socket base;
    (ii) a socket body where the aperture is located at the center of the body;
    (iii) a movable sleeve encircling the body;
    (iv) at least one retention ball;
    (v) retention apertures in the body to mate with the balls;
    (vi) a spring between the body and the sleeve; and
    (vii) having a means for puncturing (45) the end seal of the male fitting plug
    wherein the connection device is fundamentally a releasable connection system for connecting two sections of tubing together or tubing to a medical device and the device may be used for oxygen humidity bottles and other medical devices to ensure a fast, secure and hygienic connection for air, gas and liquid applications in medical applications.

* * * * *